(12) United States Patent
Oberhauser et al.

(10) Patent No.: US 8,366,220 B2
(45) Date of Patent: Feb. 5, 2013

(54) REFRIGERATOR AND/OR FREEZER

(75) Inventors: Florian Oberhauser, Graz (AT); Markus Köfele, Hopfgarten (AT)

(73) Assignee: Liebherr-Hausgeräte Lienz GmbH, Lienz (AT)

( * ) Notice: Subject to any disclaimer, the term of this patent is extended or adjusted under 35 U.S.C. 154(b) by 392 days.

(21) Appl. No.: 12/602,878

(22) PCT Filed: Jun. 4, 2008

(86) PCT No.: PCT/EP2008/004453
§ 371 (c)(1), (2), (4) Date: Dec. 3, 2009

(87) PCT Pub. No.: WO2008/151747
PCT Pub. Date: Dec. 18, 2008

(65) Prior Publication Data
US 2010/0176701 A1    Jul. 15, 2010

(30) Foreign Application Priority Data

Jun. 9, 2007    (DE) ................... 20 2007 008 106 U

(51) Int. Cl.
*A47B 96/04* (2006.01)
(52) U.S. Cl. ........................... 312/405; 312/325; 16/368
(58) Field of Classification Search .................. 16/368; 312/405, 406, 325, 326–329, 223.6; 62/389; 248/278.1, 284.1, 292.11, 160, 162.1, 123.11, 248/421, 917
See application file for complete search history.

(56) References Cited

U.S. PATENT DOCUMENTS

| | | | | |
|---|---|---|---|---|
| 2,778,000 A * | 1/1957 | Mills | ............... | 439/31 |
| 4,609,234 A * | 9/1986 | Naniwa et al. | ............... | 312/296 |
| 4,625,936 A * | 12/1986 | Hadden, Sr. | ............... | 248/544 |
| 4,825,395 A * | 4/1989 | Kinser et al. | ............... | 361/679.09 |
| 5,195,215 A * | 3/1993 | Kiefer | ............... | 16/387 |
| 5,471,709 A * | 12/1995 | Lanzani | ............... | 16/238 |
| 5,941,619 A * | 8/1999 | Stieben et al. | ............... | 312/223.6 |
| 6,168,341 B1 * | 1/2001 | Chene et al. | ............... | 403/76 |
| 6,315,249 B1 * | 11/2001 | Jensen et al. | ............... | 248/65 |
| 6,896,344 B2 * | 5/2005 | Tsutsumi et al. | ............... | 312/330.1 |
| 7,054,147 B2 * | 5/2006 | Maatta et al. | ............... | 361/679.27 |
| 7,253,774 B2 * | 8/2007 | Kasamatsu et al. | ............... | 343/702 |
| 7,698,785 B2 * | 4/2010 | Bennett | ............... | 16/369 |
| 7,966,698 B2 * | 6/2011 | Barnett | ............... | 16/367 |
| 2002/0002758 A1 * | 1/2002 | Stura et al. | ............... | 16/287 |
| 2006/0017361 A1 | 1/2006 | Rendel et al. | | |

FOREIGN PATENT DOCUMENTS

| | | |
|---|---|---|
| DE | 3510670 | 9/1986 |
| DE | 4122541 | 1/1992 |
| EP | 0088670 | 9/1983 |
| EP | 1191289 | 3/2002 |
| WO | 2004/048865 | 6/2004 |

* cited by examiner

*Primary Examiner* — Hanh V Tran
(74) *Attorney, Agent, or Firm* — Dilworth & Barrese, LLP.

(57) ABSTRACT

A household appliance has an arrangement for guiding a cable from a body of a furniture element or appliance to a closure element, which can be swivelled relative to the body by a hinge and by which the body can be closed. This arrangement includes at least one first holding member and at least one second holding member for guiding the cable. The first holding member is arranged on a first part of the hinge and the second holding member is arranged on a second part of the hinge which is movable relative to the first hinge part.

12 Claims, 4 Drawing Sheets

REFRIGERATOR AND/OR FREEZER

BACKGROUND OF THE INVENTION

The present invention relates to an arrangement for guiding a cable from a body of a furniture element or appliance to a closure element which can be swivelled relative to the body by means of a hinge and by means of which the body can be closed.

In numerous household appliances, such as refrigerators and/or freezers, it is frequently necessary to use displays in the door or flap. To supply such displays with power and/or data, it is required to lay one or more cables from the body of the appliance into the door or flap.

SUMMARY OF THE INVENTION

It is the object underlying the present invention to provide an arrangement as mentioned above, in which the cable or cables withstand numerous opening and closing movements of the door or flap and thus in particular the likelihood for the occurrence of fatigue fractures is reduced.

This object is solved by an arrangement with the features herein. Accordingly, it is provided that the arrangement includes at least one first holding member and at least one second holding member for guiding the cable, wherein the first holding member is arranged on a first part of the hinge and wherein the second holding member is arranged on a second part of the hinge, which is movable relative to the first part of the hinge. The holding members are configured such that they guide the cable such that an opening and closing movement of the closure element is possible without the same being impeded by the cable and without the cable being exposed to great loads. Preferably, it is provided that the holding members are arranged such that during the opening or closing movement of the hinge the cable only is exposed to elastic deformations, which prevents fatigue fractures or at least reduces the likelihood for the occurrence thereof. The holding members can include for instance grooves or clamps or the like, by which the cable is guided.

The first and/or second holding member can be screwed to the first or second part of the hinge or be fixed by a plug connection.

It is conceivable that the hinge includes a body fitting and a closure element fitting and that the first and/or the second part of the hinge is formed by the body fitting and/or the closure element fitting. It is possible, for instance, that the second holding member is connected with the closure element fitting by a plug connection, i.e. is connected with that fitting which in the mounted condition of the hinge is connected with the closure element, i.e. for instance with the door or flap.

Furthermore, it can be provided that the hinge includes a body fitting and a closure element fitting as well as one or more connecting elements arranged between body fitting and closure element fitting and that the first and/or the second part of the hinge is formed by the at least one connecting element. These connecting elements can be configured as levers which are pivotally connected with each other and/or with the body fitting and/or with the closure element fitting. It is conceivable for instance that the first holding member is connected with one of these connecting elements by a screw connection.

In a further aspect of the invention it can be provided that the first holding member and the second holding member have cable guide regions which are at least partly arranged at the same level. This configuration of the invention provides for making the portions of the cable between the first and the second holding member rather short.

The first holding member and/or the second holding member can have a groove-like portion which is arranged such that in the open condition of the closure element a first portion of the cable is accommodated in the groove and in the closed condition a second portion is accommodated in the groove, which second portion is longer than the first portion. It is conceivable for instance that in the open condition of the closure element the cable is not accommodated in the groove or only with a portion which is shorter than the portion of the cable accommodated in the groove in the closed condition of the closure element.

The groove-like portion of the first holding member can extend for instance over an angle of 180°. Other groove configurations are of course also conceivable.

In a further aspect of the invention, the second holding member includes a groove-like portion which has a first region and a second region extending parallel or substantially parallel thereto as well as a U-shaped portion which connects the first region with the second region. It is conceivable that in the open condition of the closure element the cable is accommodated in the first region of the groove-like portion in a length smaller than the length in which the cable is accommodated in the first region of the groove-like portion in the closed condition.

Preferably, the first region, the second region and the U-shaped portion lie in one plane.

Furthermore, it can be provided that this plane extends vertical to the plane in which the groove of the first holding member extends.

The holding members can be configured such that in the closed condition of the closure element the terminal region of the groove-like portion of the first holding member is flush with the initial region of the groove-like portion of the second holding member.

It is conceivable that the portion of the cable which extends between the first and the second holding member is longer in the open condition of the closure element than in the closed condition of the closure element. The length of the free cable portion, which extends between the holding members and which is accommodated in none of the groove-like portions, thus can depend on the opening or closing condition of the closure element.

Furthermore, it can be provided that the first and the second holding member are arranged such that in the closed condition of the closure element they have a smaller distance to each other than in the open condition of the closure element.

The present invention furthermore relates to a household appliance with at least one arrangement according to the description herein. The household appliance for instance is a refrigerator and/or freezer.

BRIEF DESCRIPTION OF THE DRAWINGS

Further details and advantages of the invention will be explained in detail with reference to an embodiment illustrated in the drawing, in which:

FIGS. 1 and 2 show a multi-joint hinge of a refrigerator, by means of which the refrigerator door can be swivelled relative to the appliance body.

DESCRIPTION OF THE PREFERRED EMBODIMENTS

Figure 1:
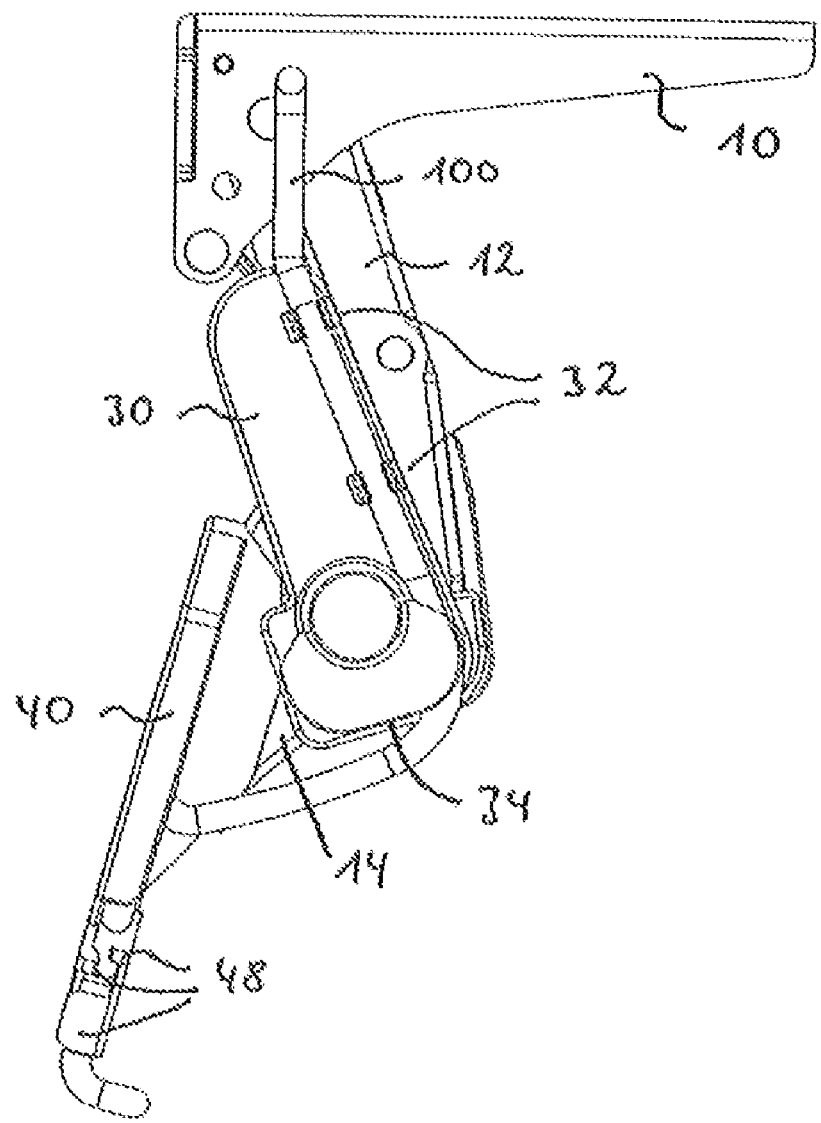
FIGS. 1, 2: show a top view and a perspective view of the arrangement in accordance with the invention when the closure element is open.

The multi-joint hinge includes a body fitting 10 which in the mounted condition of the hinge is connected with the appliance body and preferably is screwed to the same. Reference numeral 20 designates a door fitting which in the mounted condition of the hinge is connected with the door and preferably is screwed to the same.

Reference numerals 12 and 14 designate two levers, of which the lever 12 is pivotally connected with the body fitting 10 and with the lever 14 and the lever 14 is pivotally connected with the lever 12 and with the door fitting 20.

For guiding the cable 100 over the hinge, a first holding member 30 and a second holding member 40 are provided. The first holding member 30 is screwed to a bore with centering hole arranged in the lever 12. The second holding member 40 is pushed onto the door fitting 20, i.e. onto the hinge plate to which the door is screwed.

Both the first holding member 30 and the second holding member 40 are made of plastics, but other materials can also be used.

Figure 3:
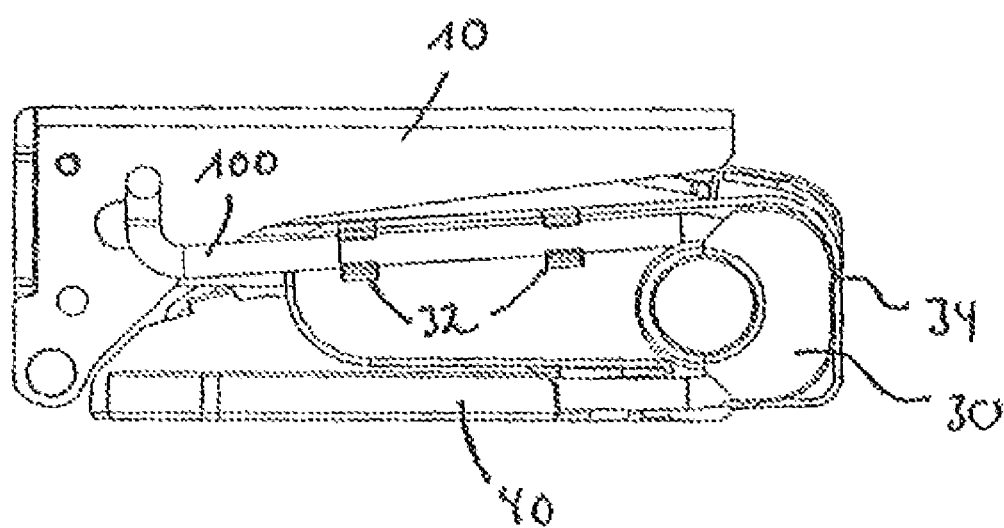
FIGS. 3, 4: show a top view and a perspective view of the arrangement in accordance with the invention when the closure element is closed.
Figure 4:
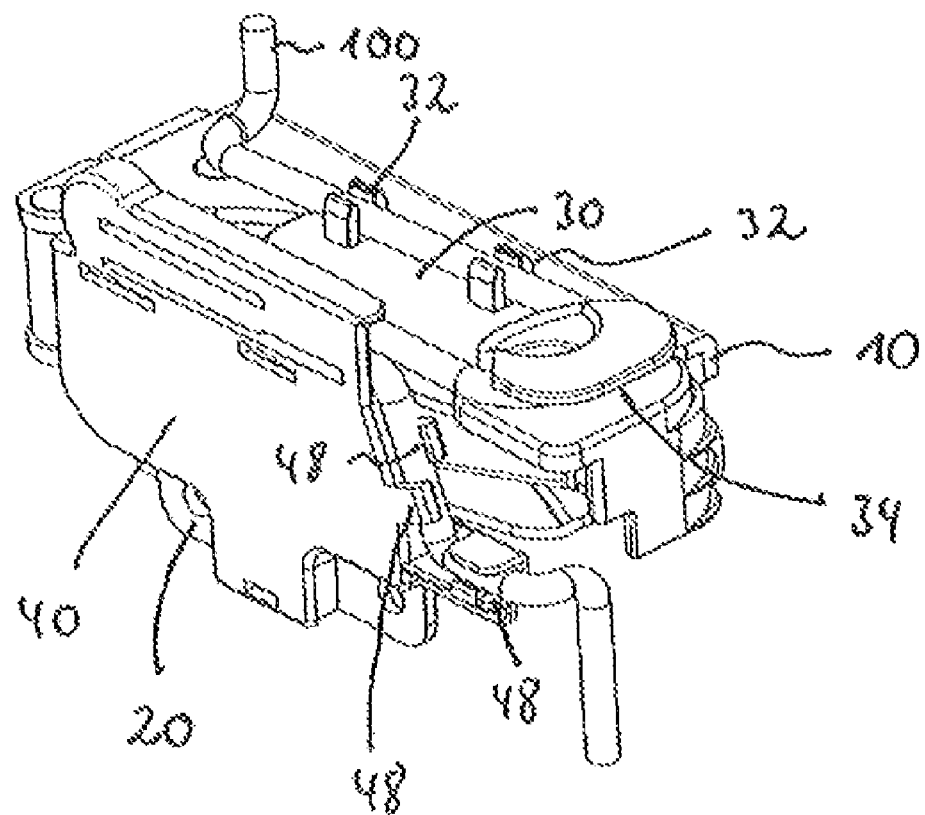

On its upper surface, the first holding member 30 has two clamps 32 between which the cable 100 is fixed. The first holding member 30 furthermore has a groove-like portion 34, into which the cable 100 fixed by the clamps 32 extends. The groove-like portion 34 extends over an angular range of 180°. As can be taken from FIGS. 3 and 4, which show the arrangement in the closing position of the closure element, the cable 100 lies in the groove-like portion 34 over said angular range of 180° when the hinge is closed. As can be taken from FIGS. 1 and 2, this does not apply in the open condition, in which the cable only rests in the initial region of the groove-like portion 34 and proceeds therefrom to extend to the second holding member 40.

The second holding member 40 has a groove-like portion with a first region 42 and a second region 44, which extend parallel to each other. Both regions are connected with each other via the U-shaped portion 46. When the hinge or the closure element is closed, the cable lies in the groove-like portion of the second holding member 40 along the entire length of the first region 42, the U-shaped portion 46 and the second region 44. In this case, the terminal region of the groove-like portion 34 of the first holding member 30 and the initial region of the groove-like portion or of the first region 42 lie adjacent to each other, so that only a comparatively short portion of the cable 100 is guided in none of the groove-like portions 34, 42.

Figure 2:
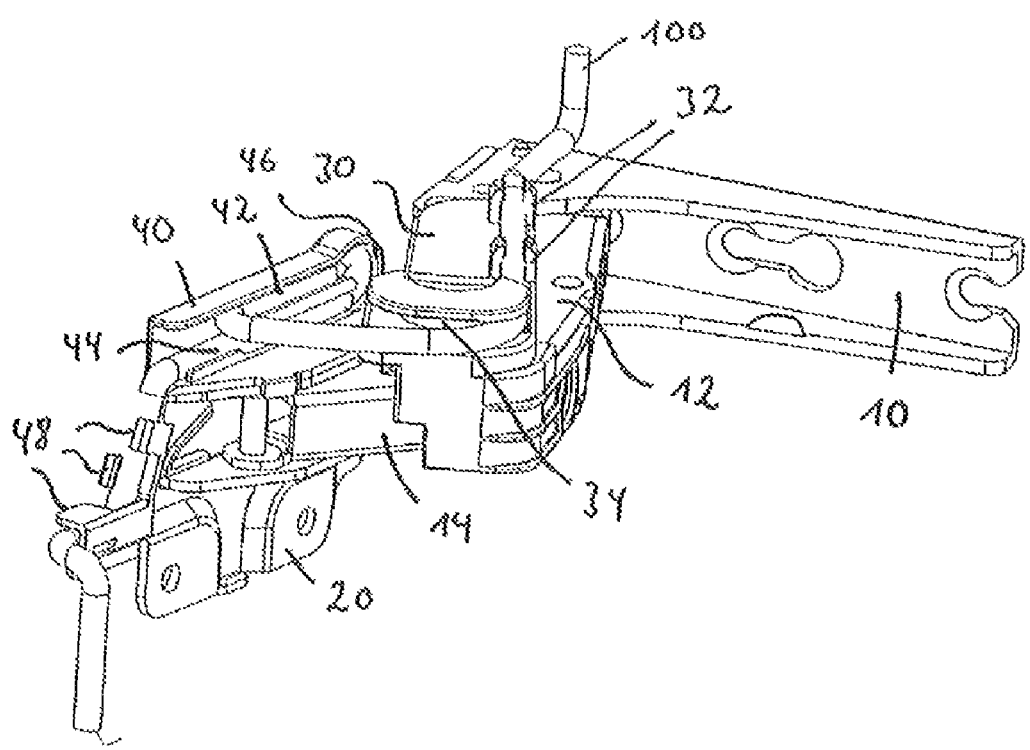

When the closure element and hence also the hinge is opened, the cable partly is removed from the groove-like portion 34 of the first holding member 30 and from the first region 42 of the second holding member 40 and extends in a straight line between the two holding members 30, 40, as can be taken from FIGS. 1 and 2.

Subsequent to the second region 44 of the second holding member 40, the cable 100 is guided by means of clamps 48 of the second holding member 40 such that it extends on to a graphic display or the like arranged in the door.

As can be taken from the Figures, the individual parts of the cable guide are constructed such that squeezing or pinching of the cable is prevented. During movement, the cable is bent around great radii, whereby kinking of the cable is prevented. As stated, the cable is applied against large curvatures when the hinge is folded or closed, which curvatures prevent the cable from being kinked or being moved within too narrow radii. The arrangement in accordance with the invention provides for performing a large number of opening and closing movements without damaging the cable.

The arrangement preferably is configured such that it can also subsequently be mounted to an already existing hinge. Preferably, it is provided that the holding members can be mounted without it being necessary to demount the hinge.

The invention claimed is:

1. A household appliance with at least one arrangement for guiding a cable (100) from a body of a furniture element or appliance to a closure element which is swivelable relative to the body by a hinge and by which the body can be closed, wherein
    the arrangement includes at least one first holding member (30) and at least one second holding member (40) for guiding the cable (100),
    the first holding member (30) is arranged on a first part (12) of the hinge and the second holding member (40) is arranged on a second part (14) of the hinge which is movable relative to the first part (12) of the hinge,
    the hinge includes a body fitting (10), a closure element fitting (20) and connecting elements (12, 14) arranged between the body fitting (10) and closure element fitting (20), and
    the first and second parts (12, 14) of the hinge are formed by the connecting elements (12, 14).

2. The appliance according to claim 1, wherein the first (30) and the second holding member (40) are respectively screwed to the first (12) or second part (14) of the hinge or fixed by a plug connection.

3. The appliance according to claim 1, wherein the first holding member (30) and the second holding member (40) include cable guide regions which are at least partly arranged at the same level.

4. The appliance according to claim 1, wherein the first holding member (30) and the second holding member (40) each have a groove-like portion (34; 42, 44, 46) which is arranged such that in the open condition of the closure element, a portion of the cable (100) is accommodated in the groove-like portions (34; 42) of said holding members (30, 40) and in the closed condition, a longer portion of the cable (100) is accommodated in the groove-like portions (34; 42) of said holding members (30, 40).

5. The appliance according to claim 4, wherein the groove-like portion (34) of the first holding member (30) extends over an angle of 180°.

6. The appliance according to claim 1, wherein the second holding member (40) has a groove-like portion (42, 44, 46) which includes a first region (42) and a second region (46) extending parallel or substantially parallel thereto and a U-shaped portion (44) which connects the first region (42) with the second region (46).

7. The appliance according to claim 6, wherein the first region (42), the second region (44) and the U-shaped portion (46) lie in one plane.

8. The appliance according to claim 7, wherein the plane is vertical to the plane in which a groove-like portion (34) of the first holding member (30) extends.

9. The appliance according to claim 4, wherein in the closed condition of the closure element the terminal region of the groove-like portion (34) of the first holding member (30) is flush with the initial region of the groove-like portion (42) of the second holding member (40).

10. The appliance according to claim 1, wherein the first (30) and the second holding member (40) are arranged such that in the closed condition of the closure element they have a smaller distance to each other than in the open condition of the closure element.

11. The household appliance according to claim 1, wherein the household appliance is a refrigerator or freezer or combination of a refrigerator and freezer.

12. An arrangement for guiding a cable (100) from a body of a furniture element or appliance to a closure element which is swivelable relative to the body by a hinge and by which the body can be closed, wherein the arrangement includes at least one first holding member (30) and at least one second holding member (40) for guiding the cable (100), the first holding member (30) is arranged on a first part (12) of the hinge and the second holding member (40) is arranged on a second part (20) of the hinge which is movable relative to the first part (12) of the hinge, said first and second hinge parts (12, 20) are coupled together along a pivot axis, said first and second holding members (30, 40) are separately-mounted apart from one another on said respective first and second hinge parts (12, 20), and said first and second holding members (30, 40) each comprise both clamps (32, 48) and a continuous groove-like portion (34; 42, 44, 46) separately-arranged along a path for the cable (100), for receiving and retaining the cable (100) therein.

* * * * *